even pages in length.

United States Patent [19]

Newman et al.

[11] Patent Number: 4,552,153

[45] Date of Patent: Nov. 12, 1985

[54] PRESSURE GAUGE

[75] Inventors: Richard W. Newman; John D. Connors, both of Auburn; Andrew J. Kugler, Camillus, all of N.Y.; Herbert H. Loeffler, Arlington, Mass.

[73] Assignee: Welch Allyn Inc., Skaneateles Falls, N.Y.

[21] Appl. No.: 552,693

[22] Filed: Nov. 17, 1983

[51] Int. Cl.$^4$ .............................................. A61B 5/02
[52] U.S. Cl. ................................... 128/677; 128/685; 73/715; 73/744
[58] Field of Search ................ 128/677, 672, 680–683, 128/685; 73/740, 744, 715

[56] References Cited

U.S. PATENT DOCUMENTS

| | | | |
|---|---|---|---|
| 3,613,667 | 10/1971 | Beck | 128/677 |
| 3,738,357 | 6/1973 | Hayes | 128/685 |
| 3,823,707 | 7/1974 | Hayes | 128/685 |
| 3,901,217 | 8/1975 | Clark | 128/677 |
| 4,010,739 | 3/1977 | Leach | 128/677 |
| 4,013,265 | 3/1977 | Speidel | 128/685 X |
| 4,128,014 | 12/1978 | Enatsu | 128/677 X |
| 4,243,201 | 1/1981 | Speidel | 128/685 X |

FOREIGN PATENT DOCUMENTS

| | | | |
|---|---|---|---|
| 0079617 | 5/1983 | European Pat. Off. | 128/672 |
| 2840475 | 8/1980 | Fed. Rep. of Germany | 128/672 |

Primary Examiner—Lee S. Cohen
Assistant Examiner—Angela D. Sykes
Attorney, Agent, or Firm—Bruns and Wall

[57] ABSTRACT

A blood pressure measuring device including a housing, a rubber bulb connected to the housing for providing fluid under pressure to a cuff and a gauge on the housing for indicating the pressure of the fluid in the cuff. In the housing there is a piston and rolling diaphragm assembly arranged so that the piston is moved by the fluid under pressure. The piston in turn moves the free end of a leaf spring operatively connected to the gauge needle whereby movement of the piston causes the needle to rotate with respect to its dial. The leaf spring is engaged by an adjustable fulcrum that can be moved on one axis to adjust for the zero setting of the gauge needle and on another axis to control the spring rate of the spring. By controlling the spring rate, the gauge can be accurately calibrated. The adjustments for the fulcrum are accesible from the exterior of the housing. The device also includes a valve for bleeding the fluid under pressure and a trigger element for operating the valve. The valve is provided with a double O-ring seal to minimize the possibility of fluid leakage when the valve is closed. The trigger element is connected through a cam follower to a cam having a configuration that gives the trigger a push-to-lock and a push-to-release action, the lock position of the trigger being used for a quick bleed or "dumping" capability.

24 Claims, 16 Drawing Figures

4,552,153

PRESSURE GAUGE

BACKGROUND OF THE INVENTION

This invention relates generally to pressure measuring apparatus, and has particular reference to a novel construction for a blood pressure measuring device or sphygmomanometer, which construction results in an efficient and very accurate instrument.

A relatively large number of blood pressure measuring devices have been developed over the years with some very advantageous designs having been provided. A problem with even some of the best designs, however, has been that of achieving and maintaining accurate calibration, including precise zero settings for indicator gauges. This means that if in a periodic test an instrument is found to be inaccurate it must be returned to the factory for recalibration which obviously is an inconvenience. Other problems that have occurred in prior art devices involve obtaining satisfactory bleed valve performance and achieving fluid tight integrity within the device.

The closest prior art known to the applicants is disclosed in U.S. Pat. Nos. 3,738,357, issued June 12, 1973 to Roger Hayes; 3,823,707, issued July 16, 1974 to Roger Hayes; 4,013,265, issued Mar 22, 1977 to B. Speidel and 4,243,201, issued Jan. 6, 1981 to B. Speidel. These patents are chiefly directed to bleed valve performance and do not disclose a piston and rolling diaphragm assembly, as taught by the present invention, for moving the gauge needle in response to fluid pressure in the blood pressure cuff. The cited prior art also lacks externally accessible calibration adjustments as disclosed herein which adjustments enable the physician to maintain accurate calibration in his blood pressure measuring device without the need to return it to the factory. Other differences between the construction of the device of the invention and those of the prior art will become apparent as the description proceeds.

SUMMARY OF THE INVENTION

The blood pressure measuring device of the invention is used in conjunction with a conventional blood pressure cuff and includes a housing, a rubber bulb connected to the housing for providing fluid under pressure to the cuff and a gauge on the housing for indicating the pressure of the fluid in the cuff, the gauge having the usual dial and needle. Within the housing, there is a piston and rolling diaphragm assembly that is arranged so that the piston is moved by the fluid under pressure. This piston in turn moves the free end of a leaf spring that is operatively connected to the gauge needle whereby movement of the piston causes the needle to rotate with respect to its dial.

The leaf spring is engaged by adjustable fulcrum means that can be moved on one axis to adjust for the zero setting of the gauge needle and on another axis to control the spring rate of the spring. By controlling the spring rate, the gauge can be accurately calibrated. The means for adjusting the fulcrum are accessible from the exterior of the housing so that the physician or a technician can make any adjustments that are needed.

The blood pressure measuring device also includes a valve for bleeding the cuff and housing of the fluid under pressure and a trigger element for operating the valve. The valve is provided with a double O-ring seal to minimize the possibility of fluid leakage when the valve is closed. The trigger element is connected through a cam follower to a cam having a configuration that gives the trigger a push-to-lock and a push-to-release action, the lock position of the trigger being used when it is desired to have a quick bleed or "dumping" capability.

DESCRIPTION OF THE PREFERRED EMBODIMENT

Figure 1:
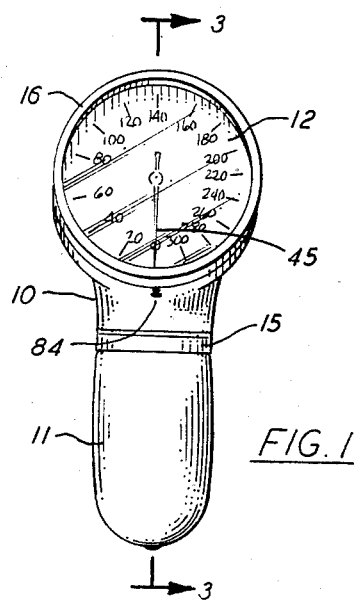
FIG. 1 is a front elevation of a blood pressure measuring device embodying the invention.

Having reference now to the drawings, the blood pressure measuring device is essentially comprised of a housing 10, a rubber squeeze bulb 11 and a conventional type pressure gauge dial 12. The housing consists of left and right mating halves that are preferably molded plastic. The two halves are secured together by a snap ring 14, FIG. 3, a threaded collar 15 and the gauge bezel 16.

Figure 3:
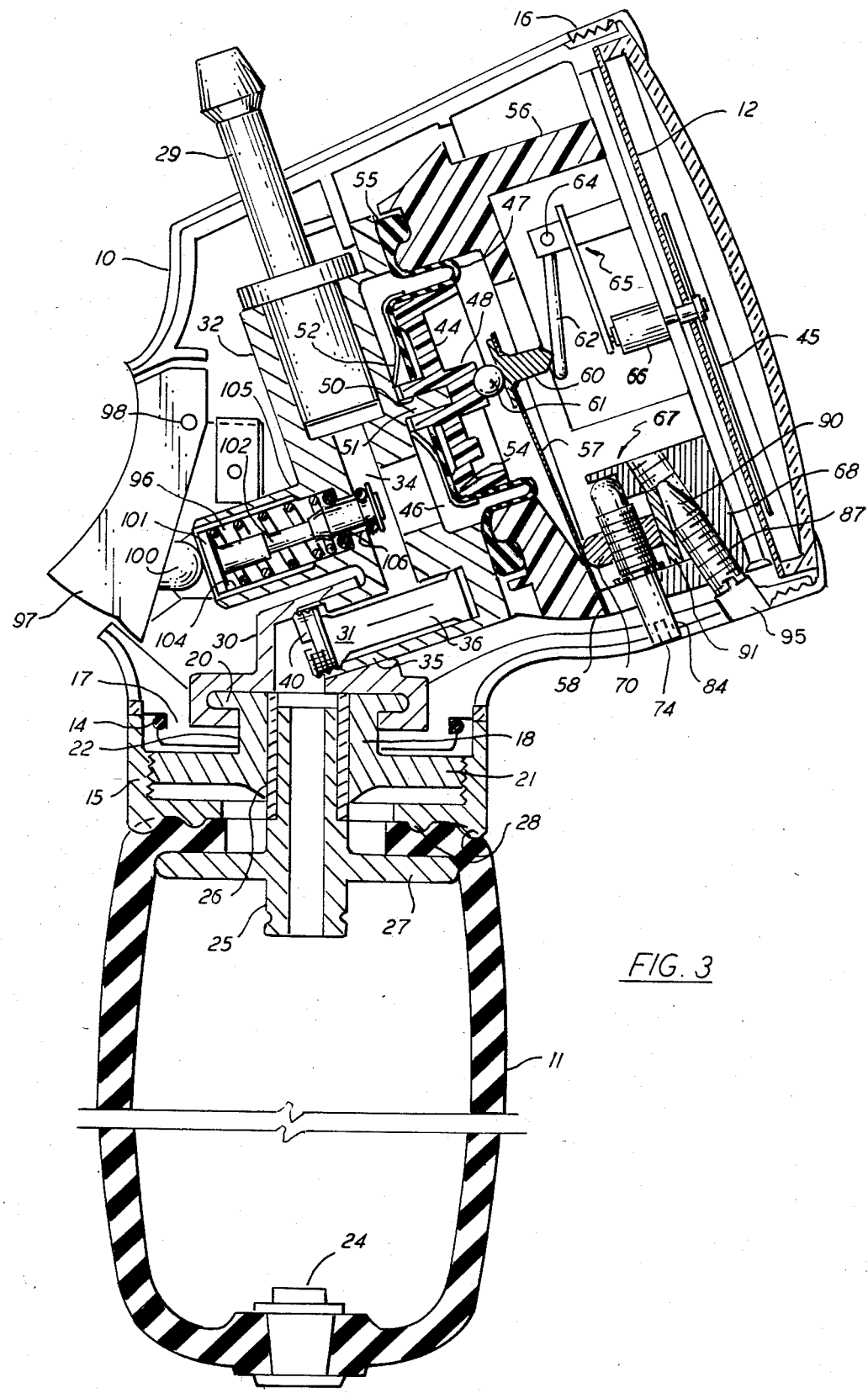
FIG. 3 is an enlarged vertical section through the device taken substantially on line 3—3 of FIG. 1.

Mounted in the lower wall 17 of the housing, FIG. 3, is a collar adapter 18 having upper and lower flanges 20 and 21. The portion of the adapter between these flanges is flatted on opposite sides and is received in a conforming opening 22 in the housing lower wall. With this arrangement, the adapter 18 is non-rotatably connected to the housing and the collar 15 is threaded onto the lower flange 21 of the adapter as shown.

The rubber squeeze bulb 11, which has a conventional check valve 24 in its bottom wall, FIG. 3, is secured to the housing by means of a tubular bulb connector element 25 the upper end of which is threaded into a tapped passage 26 in the collar adapter 18. To this end, the bulb connector is provided with an annular flange 27 and the apertured top wall of bulb 11 is squeezed between this flange and the underside of collar 15 so that a fluid tight seal is effected. To help insure such a seal, the underside of the collar is formed with annular protuberances 28 which project into the bulb wall.

Figure 2:
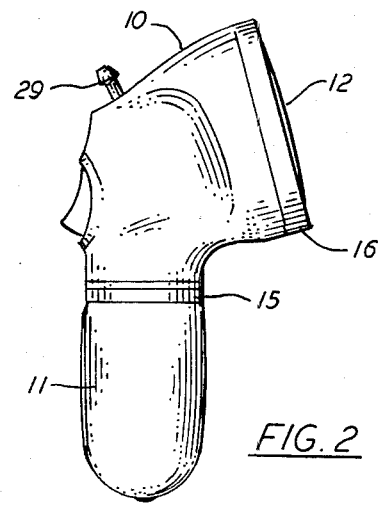
FIG. 2 is a side elevation of the device.
Figure 4:
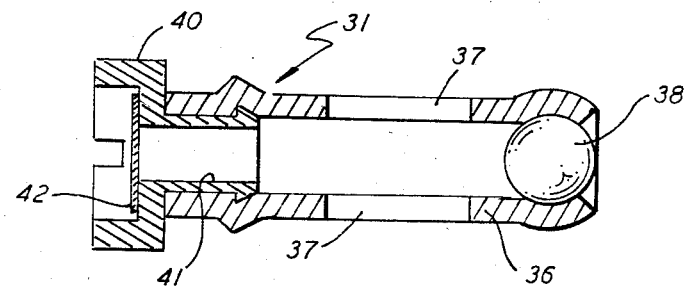
FIG. 4 is an enlarged longitudinal section through the check valve assembly.

As shown in FIGS. 2 and 3, the blood pressure measuring device is provided at its top with a tubular stem 29 that is adapted to be connected in a fluid tight manner to a conventional, inflatable blood pressure cuff (not shown). When the rubber bulb 11 is squeezed in the usual manner to inflate the cuff, the air passes up through the tubular connector element 25, through a rubber boot 30 and into a check valve assembly 31, FIGS. 3 and 4, to be described. The valve assembly 31 is located in the lower part of a valve block 32 that is suitably supported in the housing interior. The air leaving the check valve passes up through a passage 34 in the valve block into the stem 29 and from thence to the cuff.

The lower end of the rubber boot 30, FIG. 3, encircles the upper flange 20 of the collar adapter and the upper end of the boot encircles a cylindrical projection 35 on the valve block in which the check valve assembly 31 is mounted. The boot thus insures a fluid tight connection between the bulb connector element 25 and the valve assembly. The check valve assembly, FIGS. 3 and 4, comprises a flexible silicon tube 36 having a pair of diametrically opposed, longitudinal slits 37. One end of the tube is sealed by a ball 38 while the other end is occupied by a slotted plug 40 having a longitudinal passage 41 therethrough. The outer end of this passage is covered by a filter 42. The plug is threaded into the cylindrical projection 35 on the valve block as best shown in FIG. 3.

When the bulb 11 is actuated to inflate the blood pressure cuff, the fluid pressure also acts on a piston 44, FIG. 3, that operates through a mechanism to be described to rotate the gauge needle 45. Thus, the fluid enters a chamber 46 that is in communication with the fluid passage 34 in the valve block 32. Chamber 46 is defined by the valve block, the piston 44 and a rolling diaphragm 47 that extends between the piston and valve block as shown.

Figure 5:
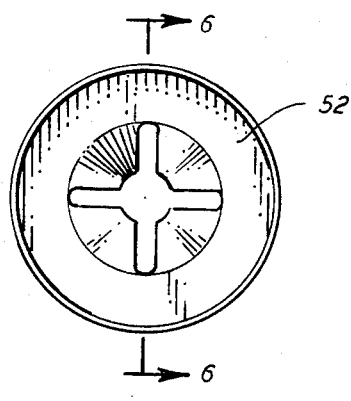
FIG. 5 is a top plan view of the diaphragm retainer.
Figure 6:
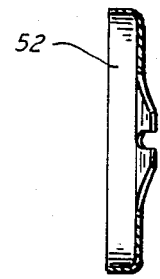
FIG. 6 is a sectional view through the retainer taken on line 6—6 of FIG. 5.

The piston 44 is formed with a central hub 48 and on one side the hub has a bore 50 which receives a cylindrical pin 51 that projects from the valve block 32. The pin is received in the bore with a sliding fit and the two coact to guide the piston in linear movement under the influence of the fluid under pressure. The central portion of the rolling diaphragm 47 overlies the piston and is formed with a center hole through which the piston hub projects. The diaphragm is maintained in contact with the piston by means of a generally cup shaped retainer 52, FIGS. 3, 5 and 6. The retainer forces the diaphragm tightly against a circumferential rib 54 on the piston so that the parts are connected together in fluid tight relation.

The diaphragm 47 is formed with a relatively large circumferential bead 55, FIG. 3, that is sandwiched in a fluid tight manner between the valve block 32 and a spring block 56. The spring block contains the mechanism for translating the linear movement of piston 44 into the angular or rotational movement of the gauge needle 45.

Figure 7:
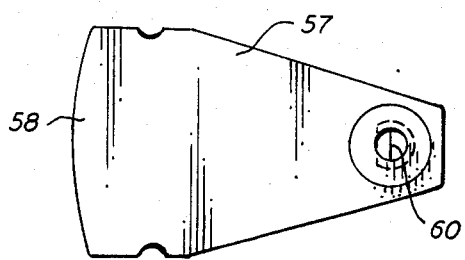
FIG. 7 is an enlarged top plan view of the leaf spring and pointer element.

A generally sector shaped leaf spring 57, FIGS. 3 and 7, is secured at its wide end 58 to the spring block 56 and projects into the block so that its free end is positioned opposite the central hub 48 of the piston. The free end of the leaf spring carries a pointer element 60 that is engaged by the piston hub through a ball bearing 61, the bearing being held in position by conforming recesses in the hub and pointer element as best shown in FIG. 3. The leaf spring opposes piston movement towards the gauge, or to the right as viewed in FIG. 3, but movement of the piston in this direction causes arcuate movement of the leaf spring free end. The translation of the piston linear movement into the arcuate movement of the spring is accommodated by the ball bearing 61.

When the leaf spring 57 moves to the right, its pointer element causes a lever 62, FIG. 3, to pivot about its pivot point 64. The movement of the lever is translated through a well known mechanism generally indicated at 65 into rotational movement of a pinion 66 that is connected to the gauge needle 45.

Figure 8:
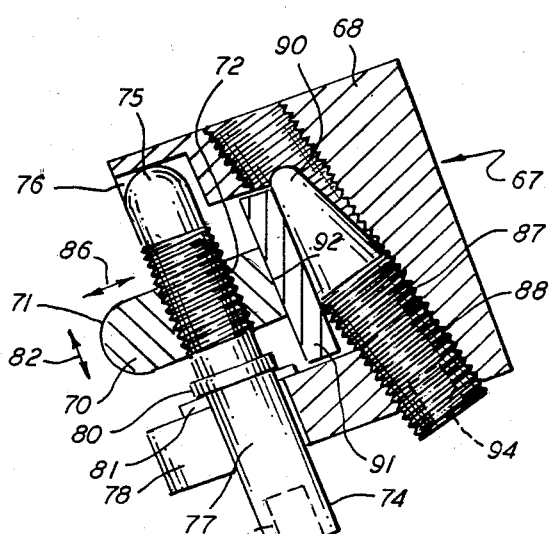
FIG. 8 is an enlarged sectional view through the adjustment mechanism.
Figure 9:
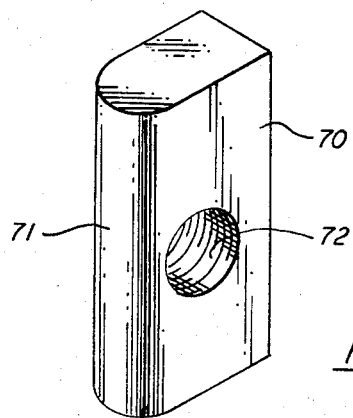
FIG. 9 is an enlarged perspective view of the fulcrum bar.

In accord with the invention, means are provided for adjusting the zero position of the gauge needle 45 and the spring rate of the leaf spring 57, this adjustment means being accessible from the exterior of the housing so that adjustments can be made by the physician without having to return the device to the factory. The adjustment mechanism, indicated generally at 67 in FIGS. 3 and 8, is assembled in an adjustment block 68 that is mounted in an opening in the side wall of spring block 56. The adjustment mechanism includes a fulcrum bar 70, FIGS. 3, 8 and 9, having a rounded side 71 that bears against the leaf spring 57 as best shown in FIG. 3.

The fulcrum bar has a transverse central bore 72 in which a spring rate adjustment screw 74 is threaded. The adjustment screw has a rounded nose portion 75, FIG. 8, that is received with a close, sliding fit in a slot 76 in the adjustment block 68. The adjustment screw is also formed with a smooth cylindrical portion 77 that is received with a close, sliding fit in a slot 78 in the adjustment block. At the inner end of the cylindrical portion 77, the adjustment screw has an integral flange 80 that bears against a washer 81. With this arrangement, lengthwise movement of the adjustment screw 74 is prevented whereby turning the screw operates to move the fulcrum bar 70 in the direction shown by the double arrow 82 in FIG. 8, or in a direction that is substantially parallel to the plane of leaf spring 57. The cylindrical portion 77 of the adjustment screw extends outwardly through a small opening 84 in the housing, FIGS. 1 and 8, and has a hexagonal socket 85 in its outer end so that it can be turned as necessary by an Allen wrench.

The fulcrum bar 70 can also be moved in the direction shown by the double arrow 86 in FIG. 8, or in a direction that is substantially perpendicular to the plane of leaf spring 57. This movement is accomplished by a zero adjustment screw 87, FIGS. 3 and 8, that is threaded into the adjustment block 68 at 88. The screw 87 has a conical inner end 90 that engages a free mounted adjustment plate 91 that in turn engages the flat inner side 92 of the fulcrum bar 70. With this arrangement, when the screw 87 is turned to advance it into the adjustment block, for example, its conical inner end acts as a wedge surface and moves the adjustment plate 91 and the fulcrum bar to the left as viewed in FIGS. 3 and 8, the adjustment screw 74 also moving with the fulcrum bar. The adjustment screw 87 has a hexagonal socket 94 in its outer end which socket is accessible through an opening 95 in the housing.

With the adjustment mechanism described above, if it is visually determined that the gauge needle 45 is not precisely on zero when the pressure in the device does not exceed atmospheric, this can be corrected by turning the zero adjustment screw 87 in or out. This slightly alters the angular position of the leaf spring 57 and this in turn operates through the lever 62, mechanism 65 and pinion 66 to adjust the position of the needle.

To determine whether the device is accurately calibrated, i.e. whether the reading on the dial is actually the fluid pressure in the cuff when the device is in use, the device must be periodically compared with a mercury manometer. If the reading on the device is inaccurate, correction can be made by turning the spring rate adjustment screw 74 in or out. Ideally, this does not alter the angular position of the leaf spring 57 but by moving the fulcrum bar along the spring, in a direction substantially parallel to the plane of the spring, the spring is made easier or more difficult to deflect. Stated another way, the position of the fulcrum controls the amount of resistance the free end of the leaf spring offers to the movement of the piston 44, and this in turn determines the extent of the angular rotation of the gauge needle for a given increment of piston movement.

Figure 10:
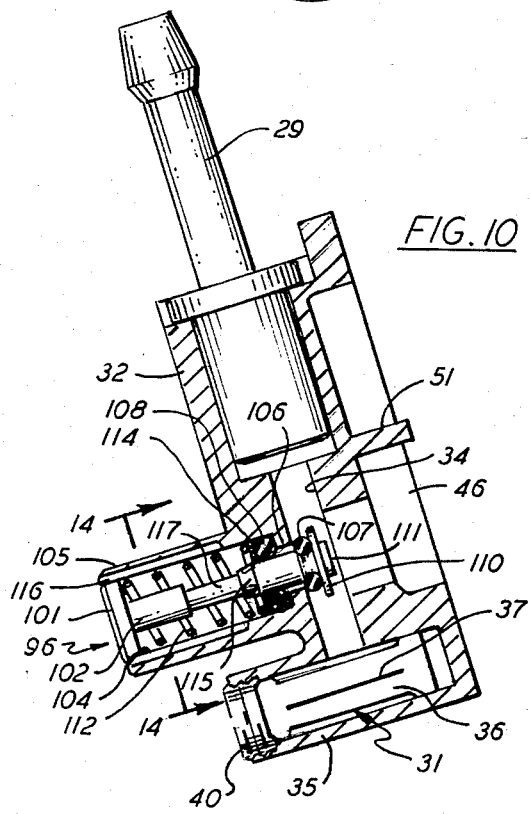
FIG. 10 is a vertical sectional view through the valve block showing the detailed construction thereof.

After the blood pressure cuff has been inflated, the cuff and device are bled of the fluid under pressure by a normally closed bleed valve generally indicated at 96 in FIGS. 3 and 10. The bleed valve is controlled by a trigger 97 that is pivotally connected to the housing at 98. Trigger 97 is formed with a rounded projection 100 near its lower end, and this projection engages the head 101 of a bleed pin 102.

The bleed pin is mounted in the bore 104 of a tubular projection 105 on the valve block 32, FIGS. 3 and 10, and the inner end of the pin passes with a clearance fit through a circular orifice 106 that connects the bore 104 with the previously described fluid passage 34 in the valve block. The inner end of the bleed pin 102 projects into the passage 34, and when the bleed valve is closed as shown in FIGS. 3 and 10, an O-ring 107 on the inner end of the pin engages the wall of passage 34 so that there is a fluid tight seal between the passage 34 and bore 104. A second O-ring 108 is mounted at the inner end of the bore 104 and provides a fluid tight seal on the periphery of the bleed pin thus providing a second seal. The O-ring 107 is retained on the bleed pin by a washer 110 and snap ring 111, FIG. 10, and is urged into close engagement with the passage wall by a compression spring 112 that encircles the bleed pin and is confined between the head 101 of the pin and a washer 114 that abuts the O-ring 108.

Figure 14:
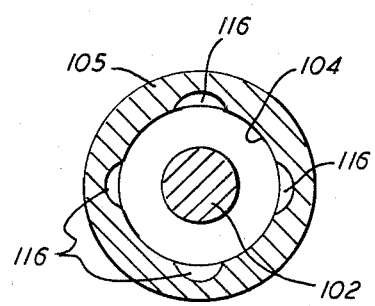
FIG. 14 is an enlarged sectional view through the bleed valve taken on line 14—14 of FIG. 10.

When the trigger 97 is pushed inwardly it lifts O-ring 107 away from its seat in passage 34 and moves a tapered portion 115 on the bleed pin through the O-ring 108 and into the orifice 106. This allows the fluid under pressure in the cuff and housing to escape at a controllable, variable rate enabling the readings to be taken. The longitudinal position of the taper 115 relative to O-ring 108 determines the size of the bleed passage and thus the bleed rate. In this connection, it can be seen from FIGS. 10 and 14 that the bore 104 is provided with longitudinal relief passages 116 whereby fluid entering the bore through the orifice 106 can escape to the atmosphere.

After the readings have been taken, quick bleeding is usually desired and this can be achieved by pushing the trigger 97 farther in which moves a reduced diameter portion 117 on the bleed pin into the orifice 106 so that the fluid can escape rapidly. However, even when the fluid is being bled quickly or "dumped", the device operator may not wish to continue squeezing the trigger. Therefore, means are provided to lock the trigger in its inner, quick bleed position.

Figure 11:
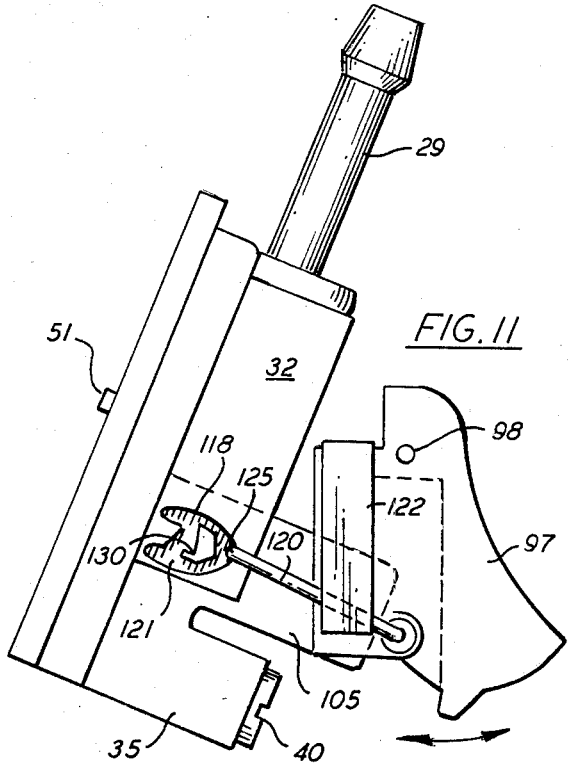
FIG. 11 is a side elevation of the opposite side of the valve block showing the interrelation between the trigger, cam and cam follower.
Figure 12:
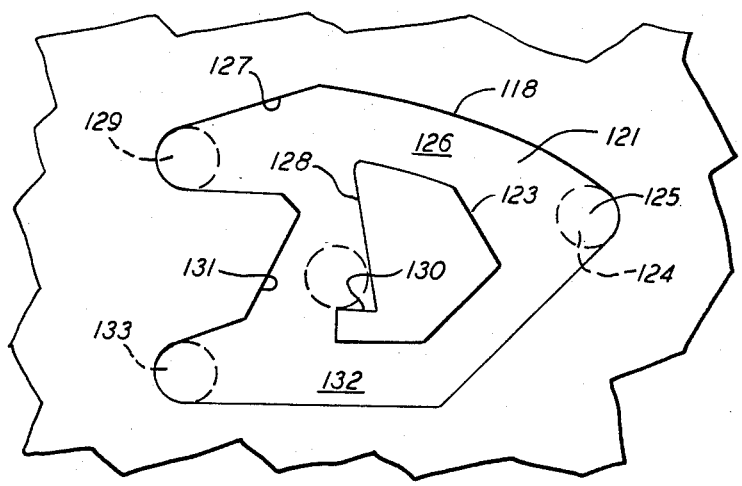
FIG. 12 is an enlarged side elevation of the cam.
Figure 13:
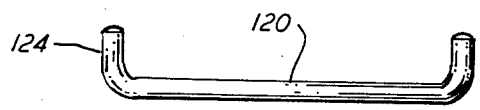
FIG. 13 is an enlarged top plan view of the cam follower.

The mechanism to lock trigger 97 in its quick bleed position is best shown in FIGS. 11, 12 and 13 and comprises a cam 118 and a cam follower 120 that connects the trigger with the cam recess or track 121. The follower is held in engagement with the trigger and cam track by an overlying leaf spring 122, FIG. 11. When the bleed valve 96 is closed and the trigger is in its normal position, the inwardly turned inner end 124 of the cam follower is positioned in the cam track at what is designated its starting point 125.

The cam track 121 is designed so that the trigger has a push-to-lock and a push-to-release action and the leaf spring 122 maintains the orientation of the cam follower 120 until the follower is acted upon by the inclines, to be described, in the cam track 121. Thus, when the trigger is pushed all the way in, the end 124 of the cam follower hits the incline 123, FIG. 12, directing it into the upper, substantially horizontal leg 126 of the cam track until it reaches the incline 127 which pushes the end down into a stop position 129. Upon release of the trigger, the end of the follower travels down the incline 128 and comes to rest in a notch 130 at the bottom of the incline. When the cam follower is in this position, the trigger is locked in its quick bleed position. The compression spring 112 biases the trigger outwardly and operates to hold the trigger in the locked position until it is again pushed to release.

When the trigger is pushed inwardly to release it from locked position, the end 124 of the cam follower encounters an incline 131 that pushes it down to a stop position 133. Upon release of the trigger, the end 124 follows leg 132 of the cam track back to the starting point 125 under the influence of the compression spring 112.

The trigger mechanism just described is an improvement over existing bleed actuators in that it is easier to actuate, more accurate in adjusting variable bleed rates, and is easier to release.

Referring again to the piston 44 and rolling diaphragm 47, FIG. 3, it should be noted that this fluid pressure responsive arrangement has a number of advantages over the metal bellows that are conventionally employed for this purpose. Thus, the rolling diaphragm permits a long piston stroke which reduces the high amplification that is usually required in the translation mechanism 65. Also, with the piston-rolling diaphragm assembly there is no need to carefully match components or adjust movements in order to change their outputs as is necessary when using metal bellows, and the leaf spring is less subject to fatigue and should stay accurate for a long time.

Figure 15:
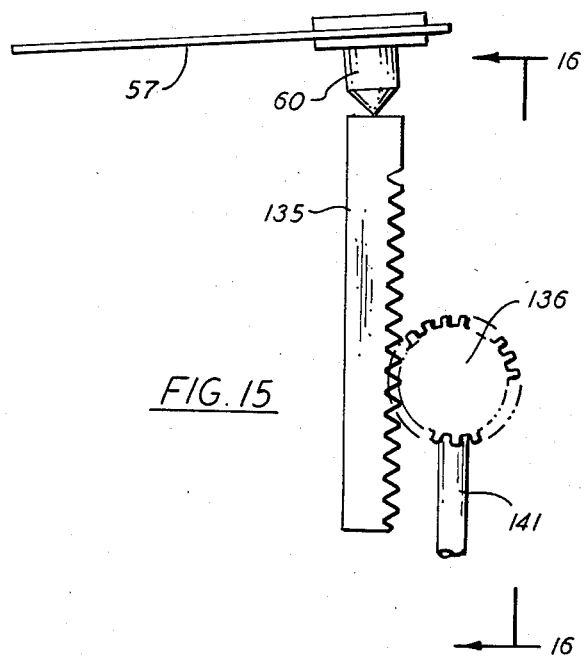
FIG. 15 is an alternative mechanism for connecting the leaf spring to the gauge needle.
Figure 16:
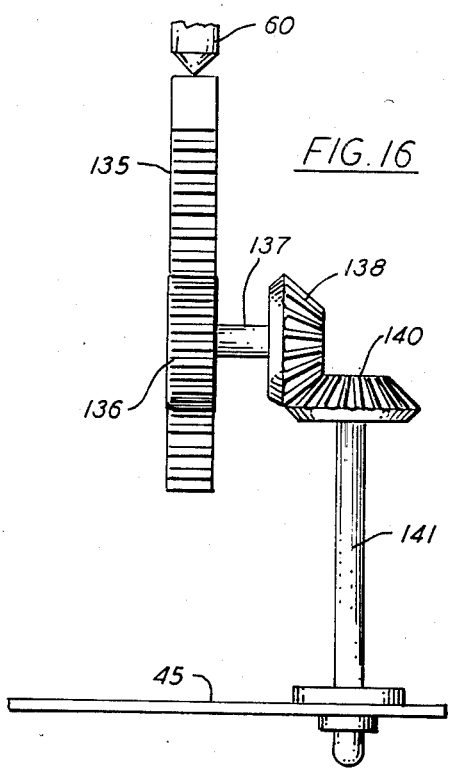
FIG. 16 is a side elevation of the mechanism of FIG. 15 looking in the direction of arrows 16—16 in FIG. 15.

FIGS. 15 and 16 illustrate an alternative mechanism for connecting the free end of leaf spring 57 to the gauge needle 45 which mechanism eliminates the time consuming and often inaccurate three-dimensional adjustment that is usually required for a conventional lever movement 65. The alternative mechanism, which requires no preliminary adjustment, includes a rack 135 and pinion 136, one end of the rack being engaged by the pointer 60 on the free end of the spring whereby the rack is moved when the leaf spring moves under fluid pressure. The rack is suitably guided in the housing for longitudinal movement and when it moves it turns the pinion 136.

The pinion is connected by a suitably journalled stub shaft 137 to a bevel gear 138. Bevel gear 138 engages a second bevel gear 140 that is connected by a shaft 141 to the gauge needle 45, the shaft 141 also being suitably journalled in the housing.

While the device disclosed herein has been described with specific reference to a sphygmomanometer or blood pressure measuring device, it will be understood by those familiar with the art that it could also be advantageously used for other pressure measuring applications as, for example, for a calibratable depth gauge for scuba diving.

From the foregoing description it will be apparent that the invention provides an advantageous blood pressure measuring device having many advantages over the prior art. As will be understood by those familiar with the art, the invention may be embodied in other specific forms without departing from the spirit or essential characteristics thereof.

We claim:

1. A fluid pressure measuring device comprising a housing; means connected to the housing for admitting fluid into the housing; a gauge on the housing which indicates the pressure of the fluid, the gauge having a dial and coacting needle; and means responsive to the fluid pressure in the housing for imparting rotational movement to the needle relative to the dial, the last-named means including a piston that is movable linearly in the housing by the fluid pressure, a leaf spring having a free end and an end fixed to the housing, the free end of the leaf spring being operatively engaged by the piston whereby linear movement of the piston causes arcuate movement of the leaf spring free end, means in the housing interconnecting the free end of the leaf spring and the gauge needle whereby the arcuate movement of the spring free end causes the needle to rotate, and movable fulcrum means engaging the leaf spring adjacent its fixed end for controlling the spring rate of the leaf spring and zero position of the gauge needle relative to the dial.

2. A fluid pressure measuring device as defined in claim 1 together with adjustment means operable to move the fulcrum means in a direction generally parallel to the leaf spring whereby the spring rate of the latter can be adjusted.

3. A fluid pressure measuring device as defined in claim 2 wherein the adjustment means is accessible from the exterior of the housing.

4. A fluid pressure measuring device as defined in claim 1 together with adjustment means operable to move the fulcrum means in a direction generally perpendicular to the leaf spring whereby the position of the gauge needle can be adjusted to read zero on the dial.

5. A fluid pressure measuring device as defined in claim 4 wherein the adjustment means is accessible from the exterior of the housing.

6. A fluid pressure measuring device as defined in claim 1 wherein the piston is connected to the housing by a flexible diaphragm member.

7. A fluid pressure measuring device as defined in claim 1 wherein the means interconnecting the free end of the leaf spring and the gauge needle is a non-adjustable gear train.

8. For use with an inflatable blood pressure cuff: a blood pressure measuring device comprising a housing; means connected to the housing for providing fluid under pressure to the cuff; a gauge on the housing which indicates the pressure of the fluid in the cuff, the gauge having a dial and coacting needle; and means responsive to the fluid pressure in the cuff for imparting rotational movement to the needle relative to the dial, the last-named means including a piston that is movable linearly in the housing by the fluid pressure, a leaf spring having a free end and an end fixed to the housing, the free end of the leaf spring being operatively engaged by the piston whereby linear movement of the piston causes arcuate movement of the leaf spring free end, means in the housing interconnecting the free end of the leaf spring and the gauge needle whereby the arcuate movement of the spring free end causes the needle to rotate, and movable fulcrum means engaging the leaf spring adjacent its fixed end for controlling the spring rate of the leaf spring and zero position of the gauge needle relative to the dial.

9. A blood pressure measuring device as defined in claim 8 together with adjustment means operable to move the fulcrum means in a direction generally parallel to the leaf spring whereby the spring rate of the latter can be adjusted.

10. A blood pressure measuring device as defined in claim 9 wherein the adjustment means is accessible from the exterior of the housing.

11. A blood pressure measuring device as defined in claim 8 together with adjustment means operable to move the fulcrum means in a direction generally perpendicular to the leaf spring whereby the position of the gauge needle can be adjusted to read zero on the dial.

12. A blood pressure measuring device as defined in claim 11 wherein the adjustment means is accessible from the exterior of the housing.

13. A blood pressure measuring device as defined in claim 8 wherein the piston is connected to the housing by a flexible diaphragm member.

14. A blood pressure measuring device as defined in claim 8 together with a movable trigger element on the housing, the trigger element being operable to bleed the cuff and housing of the fluid under pressure therewithin, and cam means in the housing coactable with the trigger element to lock the trigger element at a predetermined fluid bleed rate.

15. A blood pressure measuring device as defined in claim 14 together with a fluid bleed valve actuated by the trigger element, the valve having a dual O-ring seal to minimize the possibility of fluid leakage when the valve is closed.

16. A blood pressure measuring device as defined in claim 8 wherein the means interconnecting the free end of the leaf spring and the gauge needle is a non-adjustable gear train including a rack and a pinion.

17. For use with an inflatable blood pressure cuff: a blood pressure measuring device comprising a housing; a connector element on the housing for connecting it in a fluid tight manner to the cuff; a rubber bulb connected to the housing which provides fluid under pressure to the cuff; a gauge on the housing which indicates the pressure of the fluid in the cuff, the gauge having a dial and coacting needle; and means responsive to the fluid pressure in the cuff for imparting rotational movement to the needle relative to the dial, the last-named means including a piston that is movable linearly in the housing by the fluid pressure, a flexible diaphragm connecting the piston to the housing, an elongated leaf spring having a free end and an end fixed to the housing, the free end of the leaf spring being operatively engaged by the piston whereby linear movement of the piston causes arcuate movement of the leaf spring free end, means in the housing for translating arcuate movement of the leaf spring free end into rotational movement of the gauge needle, movable fulcrum means engaging the leaf spring adjacent its fixed end, a first adjustment means operable to move the fulcrum means in a direction generally parallel to the leaf spring whereby the spring rate of the latter can be adjusted, and a second adjustment means operable to move the fulcrum means in a direction generally perpendicular to the leaf spring whereby the gauge needle can be precisely adjusted to zero on the dial.

18. A blood pressure measuring device as defined in claim 17 wherein the first and second adjustment means are both accessible from the exterior of the housing.

19. A blood pressure measuring device as defined in claim 17 together with a movable trigger element on the housing, and a fluid bleed valve actuated by the trigger element, the valve having a dual O-ring seal to minimize the possibility of fluid leakage when the valve is closed.

20. A blood pressure measuring device as defined in claim 19 together with a cam and a cam follower connected to the trigger element, the configuration of the cam being such that the trigger element has a push-to-lock and a push-to-release operation.

21. A blood pressure measuring device as defined in claim 17 together with a threaded connector which attaches the rubber bulb to the housing, the connector exerting a compressive force on the bulb that can be increased to stop any fluid leakage that may occur.

22. A blood pressure measuring device as defined in claim 17 wherein the means for translating arcuate movement of the leaf spring free end into rotational movement of the gauge needle is a non-adjustable gear train.

23. For use with an inflatable blood pressure cuff: a blood pressure measuring device comprising a housing; a connector element on the housing for connecting it in a fluid tight manner to the cuff; a rubber bulb connected to the housing which provides fluid under pressure to the cuff; a guage on the housing which indicates the pressure of the fluid in the cuff, the gauge having a dial and coacting needle; a piston in the housing that is movable linearly in response to the fluid pressure in the cuff; a rolling flexible diaphragm interconnecting the piston and housing, the piston and diaphragm forming one side of a sealed chamber in communication with the fluid in the cuff, the rolling diaphragm enabling the piston to have a relatively long stroke; and means in the housing for translating the linear movement of the piston into rotational movement of the gauge needle.

24. A blood pressure measuring device as defined in claim 23 wherein the means for translating the linear movement of the piston into rotational movement of the guage needle includes a non-adjustable gear train having a rack and a pinion.

* * * * *